(12) United States Patent
Pfeiffer et al.

(10) Patent No.: US 7,803,122 B2
(45) Date of Patent: Sep. 28, 2010

(54) DEVICE FOR DETERMINING THE TRANSITION BETWEEN SYSTOLE AND DIASTOLE

(75) Inventors: Ulrich J. Pfeiffer, Munich (DE); Reinhold Knoll, Munich (DE); Stephan Regh, Munich (DE)

(73) Assignee: Pulsion Medical Systems AG, Munich (DE)

( * ) Notice: Subject to any disclaimer, the term of this patent is extended or adjusted under 35 U.S.C. 154(b) by 269 days.

(21) Appl. No.: 11/596,652

(22) PCT Filed: May 17, 2005

(86) PCT No.: PCT/EP2005/052258

§ 371 (c)(1),
(2), (4) Date: Jan. 5, 2007

(87) PCT Pub. No.: WO2005/112746

PCT Pub. Date: Dec. 1, 2005

(65) Prior Publication Data

US 2008/0167562 A1    Jul. 10, 2008

(30) Foreign Application Priority Data

May 17, 2004 (DE) ........................ 10 2004 024 335

(51) Int. Cl.
*A61B 5/02* (2006.01)
(52) U.S. Cl. ........................ 600/500; 600/485; 600/486
(58) Field of Classification Search ................. 600/485, 600/486, 500
See application file for complete search history.

(56) References Cited

U.S. PATENT DOCUMENTS 5,265,011 A    11/1993   O'Rourke (Continued)

FOREIGN PATENT DOCUMENTS

DE    198 14 371 A1    10/1999

(Continued)

OTHER PUBLICATIONS

Brown, Kevin. Reflections on Relativity. Mathpages.com, 1999. http://www.mathpages.com/rr/rrtoc.htm (accessed May 26, 2009).*

(Continued)

*Primary Examiner*—Patricia C Mallari
*Assistant Examiner*—Christian Jang
(74) *Attorney, Agent, or Firm*—Collard & Roe, P.C.

(57) ABSTRACT

Determining the transition between systole and diastole is important for pulse contour-analytical determination of hemodynamic, first of all cardiac output. During the temporal progression of arterial pressure P(t) on which pulse contour analysis is based, the transition between systole and diastole appears as a local minimum. This local slump of the pressure curve downward is very short and is often little recognizable in the actually measured curves due to inaccuracies conditioned by measuring techniques. It was also found that the transition between systole and diastole can be more reliably and accurately determined as the site of maximum curvature of function P(t). Consequently, the invention relates to a device having a calculation unit that comprises evaluation means for detecting the site of maximum curvature of function P(t) in a detection area between the maximum and minimum functional value of the pulse cycle as the site of transition between systole and diastole.

11 Claims, 1 Drawing Sheet

U.S. PATENT DOCUMENTS

Figure 1:
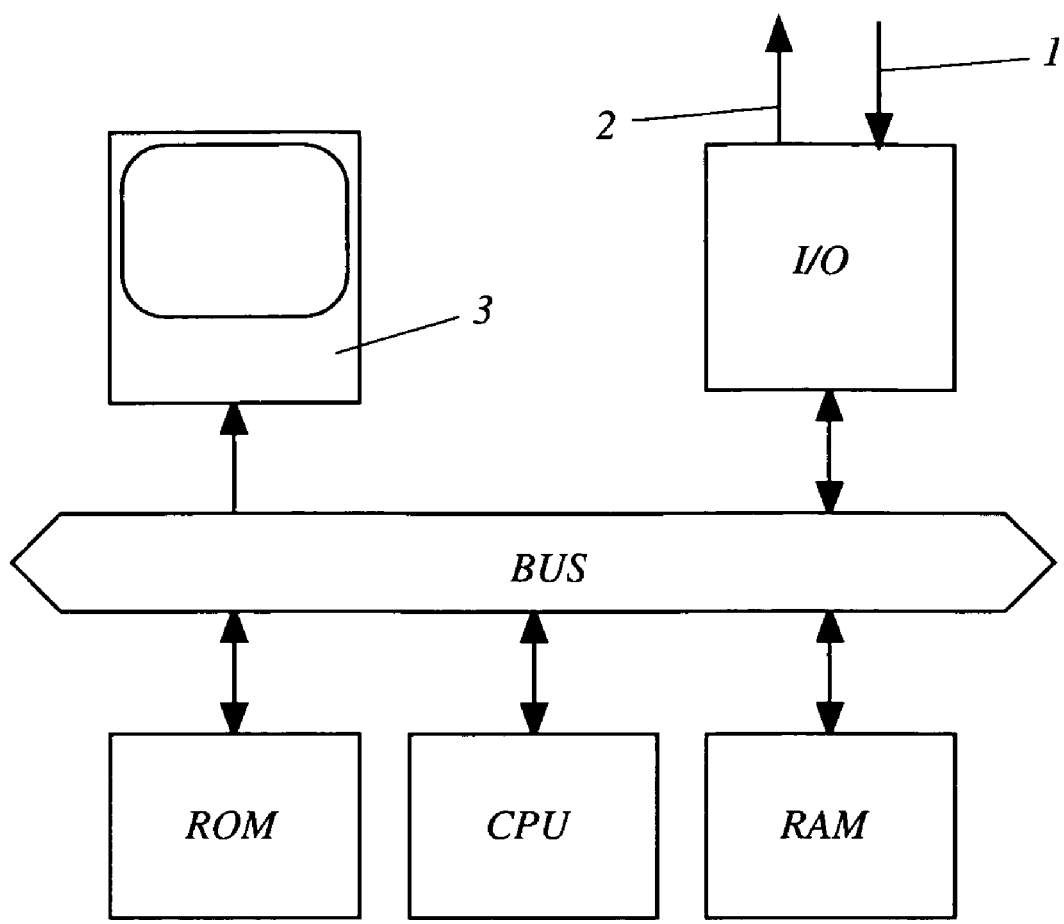

| | | |
|---|---|---|
| 6,315,735 B1 | 11/2001 | Joeken et al. |
| 6,394,958 B1 | 5/2002 | Bratteli et al. |
| 2002/0022785 A1 | 2/2002 | Romano |

FOREIGN PATENT DOCUMENTS

| | | |
|---|---|---|
| DE | 699 05 240 T2 | 2/2003 |
| EP | 1 062 596 B1 | 12/2000 |

OTHER PUBLICATIONS

International Search Report.

\* cited by examiner

DEVICE FOR DETERMINING THE TRANSITION BETWEEN SYSTOLE AND DIASTOLE

CROSS REFERENCE TO RELATED APPLICATIONS

Applicants claim priority under 35 U.S.C. §119 of German application Ser. No. 10 2004 024 335.2 filed May 17, 2004. Applicants also claim priority under 35 U.S.C. §365 of PCT/EP2005/052258 filed May 17, 2005. The international application under PCT article 21(2) was not published in English.

The present invention relates to a device for determining the transition between systole and diastole within a pulse cycle.

Determining the transition between systole and diastole (i.e. the end of the systole and the beginning of the diastole, respectively) is of particular significance in pulse contour analysis, a method for determining hemodynamic parameters, particularly cardiac output (CO) and stroke volume variation (SVV), from the time-dependent pressure signal that at least approximately corresponds to aorta pressure. Determining hemodynamic parameters by means of pulse contour analysis on the basis of a non-linear air chamber model is described in detail in DE 198 14 371 A1 as well as in the literature cited there, which goes further. A pulse contour analysis system of Pulsion Medical Systems AG is commercially available under the designation PiCCO.

As described in DE 198 14 371 A1, preferably only pressure values from the range of the diastole are used for calculating the so-called compliance, which represents an important variable for determining cardiac output, in order to accelerate the calculation process. However, this presupposes that the start of the diastole can be determined with the greatest possible precision.

In the course of the function P(t), i.e. the time progression of the pressure that approximately corresponds to the aorta pressure and forms the basis of the pulse contour analysis, the transition between systole and diastole shows itself as a local minimum, which is also referred to as the dicrotic notch. The short pressure drop is due to the fact that the aortic valve needs to close when contraction of the heart begins.

This local downward swing in the pressure curve is very short and often not very marked in curves that are actually measured, because of inaccuracies relating to measurement technology. Depending on the extent to which the underlying pressure measurements are subject to noise, it can happen that the location of the transition between systole and diastole in the pressure curve can no longer be resolved as a local minimum. This means that swings of the pressure signal caused by measurement noise lie in the same magnitude as the short-term pressure drop at the transition between systole and diastole. In this case, in practice one often makes do with determining the transition between systole and diastole approximately as the turning point of the function P(t).

In order to have to make use of this approximation only when a direct determination of the dicrotic notch as a local minimum is not possible with sufficient reliability, there is the possibility of implementing both determination methods in one system. As soon as the system recognizes that a predetermined minimum pressure drop cannot be resolved, it switches to the determination of the dicrotic notch by approximation, as the turning point of the function P(t). In other words, no differentiation between cases is made, as to whether or not a local minimum is clearly evident.

However, in practice, alternating between two algorithms can have the result that minimal changes in the measurement conditions bring with them clear changes in the calculated and displayed hemodynamic parameters: By switching from one determination method to the other, an apparent shift in the transition between systole and diastole occurs, thereby changing the data basis for all parameters that are calculated exclusively from the systolic branch or exclusively from the diastolic branch of the function P(t). Because of the "jump" in the algorithms, a physiological change that has not in fact occurred, or not occurred in the measure indicated, might be falsely shown to have happened.

In view of the set of problems described, the invention is based on the task of creating a device that allows reliable and precise determination, resistant to interference influences, of the transition between systole and diastole within the pulse cycle ("notch determination").

According to one aspect of the present invention, this task is accomplished by means of a device described herein.

Preferred embodiments of the present invention can be structured as described herein.

In the following, an example of a preferred embodiment of the invention will be explained in greater detail, using the attached drawing, which should be interpreted as being purely schematic.

In this connection, FIG. 1 shows a simplified block schematic of a device according to the invention.

The device from FIG. 1 has an input/output subsystem (I/O) having at least one input channel 1, by way of which a pressure signal that at least approximately corresponds to the aorta pressure of a patient is read in. This can be an analog sensor signal, which is digitalized by means of an analog/digital converter, or a digital signal from an external measurement transducer is already read in.

In practice, an arterial pressure advantageously measured as close to the aorta as possible, by way of an arterial catheter, serves as a pressure that approximately corresponds to the aorta pressure. A leg artery can serve as the measurement location.

The input/output system (I/O) can have one or more output or control channels 2, which can be used for calibration purposes, for example, or serve for interaction with peripherals or the like.

The components of the device that serve for signal processing are connected with one another by way of a central bus (BUS).

The pressure signal that is read in is temporarily stored in the working memory (RAM), as a function of the time P(t). The function P(t) is processed by the central processor unit (CPU), in order to calculate the transition between systole and diastole, as well as any other hemodynamic parameters, if applicable, such as cardiac output and stroke volume, from it. A corresponding control program, which causes the processor unit (CPU) to carry out the appropriate calculation steps, is stored in the fixed memory (ROM).

In this connection, determining the transition between systole and diastole by means of the processor unit (CPU) comprises the following steps.

The first ($y'=dP/dt$) and the second derivation ($y''=d^2P/dt^2$) of the function P(t) are determined using suitable smoothing algorithms.

From these, an indication function is calculated, which represents a measure of the local curvature of the function P(t). The curvature function $$K=y''/(1+y'^2)^{3/2}$$

is particularly suitable. This can be interpreted as the inverse of a local radius of curvature. The determination is improved if an axis adjustment is first provided, which lends the typical progression of an arterial pressure function approximately the shape of an arc at the transition between systole and diastole. A corresponding axis adjustment algorithm can be obtained from empirically collected data.

The location of the maximum of the curvature function K is determined within the range of the function P(t) in which the latter assumes values of 75% to 10% of its maximal value within the current pulse period. The corresponding time point is further corrected, if necessary, by taking into consideration delay elements in the measurement structure, for example filters. The determination range may extend within 90% to 10% of the maximal function value of the pulse cycle.

If the maximum of the curvature function K (after this correction, if necessary) lies within 70% of the duration of the current pulse period (or the duration of a prior pulse period, if the calculation is carried out in real time, before the end of the current pulse period), the location of the (corrected, if applicable) maximum of the curvature function K is interpreted as the time point of the transition between systole and diastole. Otherwise, the transition between systole and diastole is set at 70% of the duration of the current pulse period (or the duration of a prior pulse period, if the calculation is carried out in real time, before the end of the current pulse period).

Optionally, an additional plausibility check can also be provided, taking into consideration pulse duration, ejection time, etc.

Alternatively, it is possible to do without determining the curvature function, and instead of the maximum of the curvature function K, the maximum of the second derivation y" of the function P(t) can be interpreted as the time point of the transition between systole and diastole, if necessary after appropriate correction.

The control program in the fixed memory (ROM) can contain additional routines that enable the processor unit (CPU) to calculate additional hemodynamic factors according to known algorithms.

The function P(t) can be displayed, and the location of the transition between systole and diastole can be output, by way of a display system 3. In addition or as an alternative to this, additional hemodynamic parameters can be output.

Of course, the device can be equipped with other components known to a person skilled in the art, for example mass memory media for recording unprocessed data and/or calculated hemodynamic parameters. The processor unit (CPU) can be equipped with one or more conventional microprocessors, if necessary supported by co-processors for accelerating floating decimal point operation, or also with so-called digital signal processors (DSP). Appropriate solutions, as well as additional details of the hardware configuration, can be implemented analogous to conventional pulse contour analysis devices according to the state of the art.

The invention claimed is:

1. Device for determining the transition between systole and diastole within a pulse cycle, having an input channel for reading in a pressure signal that can change over time and at least approximately corresponds to the aorta pressure of a patient, as a function of the time P(t), and a calculation unit that has differentiation means for forming the second derivation y" from the function P(t), as well as evaluation means for determining a location of maximal curvature of the function P(t) in a determination range between the maximal and the minimal function value of the pulse cycle as the location of the transition between systole and diastole, and furthermore having differentiation means for forming the first derivation y' from the function P(t),
wherein the location of maximal curvature is defined for the evaluation means as the location of the smallest radius of curvature $$(1+y'^2)^{3/2}/y".$$

2. Device according to claim 1, which has memory means for temporary storage of the pressure signal read in, at least over the pulse cycle, as a function of the time P(t).

3. Device according to claim 1, which has filtering means for carrying out function smoothing.

4. Device according to claim 1, wherein the determination range extends within 90% to 10% of the maximal function value of the pulse cycle.

5. Device according to claim 4, wherein the determination range extends within 75% to 10% of the maximal function value of the pulse cycle.

6. Device according to claim 1, wherein the evaluation means furthermore have adaptation means for axis adjustment of the function P(t), and the axis adjustment is provided in such a manner that a typical progression of an arterial pressure function, obtained from empirically collected data, possesses approximately the shape of an arc at the transition between systole and diastole.

7. Device according to claim 1, wherein the evaluation means furthermore comprise correction means for correcting the position of the location determined for the transition between systole and diastole, in order to take delay elements into consideration.

8. Device according to claim 1, wherein the differentiation means, filter means, and evaluation means are implemented, at least in part, in terms of program technology, in the form of software.

9. Device according to claim 1, wherein the calculation unit has means for determining at least one additional hemodynamic parameter from the function P(t).

10. Device according to claim 9, having output means for outputting the hemodynamic parameters.

11. Device according to claim 1, furthermore having connection means for connecting an arterial catheter that is suitable for the pressure measurement.

* * * * *